United States Patent

Bruno

[11] Patent Number: 5,980,834
[45] Date of Patent: Nov. 9, 1999

[54] SAMPLE STORAGE DEVICES

[75] Inventor: Thomas J. Bruno, Broomfield, Colo.

[73] Assignee: The United States of America as represented by the Secretary of Commerce, Washington, D.C.

[21] Appl. No.: 08/686,462

[22] Filed: Jul. 25, 1996

[51] Int. Cl.$^6$ ..................................................... G01N 30/06
[52] U.S. Cl. ............................ 422/102; 73/1.03; 73/1.04; 73/1.06; 73/1.07; 73/23.41; 239/34; 239/53; 239/55; 239/57; 422/89; 422/101; 436/8; 436/9
[58] Field of Search ..................................... 422/101, 102, 422/89; 436/8, 9, 178; 239/34, 53, 55, 57; 73/23.41, 1.03, 1.04, 1.06, 1.07

[56] References Cited

U.S. PATENT DOCUMENTS

| | | |
|---|---|---|
| 280,820 | 7/1883 | Hickson . |
| 2,456,524 | 12/1948 | Meincke, Jr. . |
| 3,412,935 | 11/1968 | O'Keeffe . |
| 4,131,544 | 12/1978 | Elahi . |
| 4,270,921 | 6/1981 | Graas . |
| 4,332,788 | 6/1982 | Mochida et al. . |
| 4,410,085 | 10/1983 | Beneziat et al. . |
| 4,451,374 | 5/1984 | Peterson et al. . |
| 4,624,929 | 11/1986 | Ullman . |
| 4,647,380 | 3/1987 | Dasgupta . |
| 4,829,008 | 5/1989 | Zaromb . |
| 4,865,813 | 9/1989 | Leon . |
| 5,032,283 | 7/1991 | Scott et al. . |
| 5,086,642 | 2/1992 | Jessel et al. . |
| 5,187,072 | 2/1993 | Cullimore et al. . |
| 5,248,616 | 9/1993 | Beckman et al. . |
| 5,301,851 | 4/1994 | Frutin . |
| 5,334,189 | 8/1994 | Wade . |
| 5,378,360 | 1/1995 | Huse et al. . |
| 5,492,838 | 2/1996 | Pawliszyn . |
| 5,494,640 | 2/1996 | Simon et al. . |
| 5,525,475 | 6/1996 | Ladouceur . |
| 5,753,508 | 5/1998 | Robertson et al. . |
| 5,770,086 | 6/1998 | Indriksons et al. . |

*Primary Examiner*—Jan Ludlow
*Attorney, Agent, or Firm*—Dinsmore & Shohl LLP

[57] ABSTRACT

A sample storage device comprises a vial provided with an opening, a permeation tube arranged within the vial, permeable to a fluid contained in the vial or the permeation tube, and having a first closed end and an opposite second end, and a septum closure sealing the vial opening. In one embodiment, the permeation tube second end is open, the permeation tube is arranged within the vial with the second end adjacent the vial opening, and the septum closure seals the vial opening and the second open end of the permeation tube. The vial has a sample fluid, at least a portion of which is in contact with an outer surface of the permeation tube, and the permeation tube is permeable to the sample fluid. In a second embodiment, the permeation tube second end is closed, and the permeation tube includes a marker-containing adsorbent therein. The vial has a sample fluid therein and the permeation tube is permeable to the marker. In a third embodiment, the vial has a marker-containing adsorbent therein, and the permeation tube second end is open. The permeation tube contains a sample fluid and is arranged within the vial with the second open end of the permeation tube adjacent the vial opening. At least a portion of an outer surface of the permeation tube is in contact with the marker, and the permeation tube is permeable to the marker. The septum closure seals the vial opening and the second open end of the permeation tube.

15 Claims, 5 Drawing Sheets

SAMPLE STORAGE DEVICES

TECHNICAL FIELD

The present invention relates to devices and methods for long term storage and delivery of fluid samples, for example, chromatographic samples in automatic sampler vials, and for the introduction of marker compounds into such samples. More particularly, this invention relates to the use of permeation tubes through which a fluid may pass at a relatively slow, constant rate at a given temperature. The devices and methods of the invention are advantageous for the handling and storage of volatile organic compounds in that they minimize the quantities of samples needed and decrease hazards associated with the handling of such compounds. The devices and methods of the invention also allow delivery of marker compounds to chromatographic samples, whereby multiple assays may be conveniently performed, while at the same time hazards associated with the handling of such compounds are decreased and the quantity of sample required is minimized.

BACKGROUND ART

Analytical techniques are employed in many different fields for determining various properties of materials. Chromatographic analysis is one commonly used analytical technique. Automatic samplers for chromatographic analysis greatly reduce both the time and labor which are required for analysis of samples. The potential of operator exposure to dangerous or hazardous chemicals is also reduced by automatic sampler devices. However, a conventional automatic sampler container consists of a glass vial and a crimped septum cap and performs only marginally when used for analysis of volatile organic compound samples. Leakage through the septum and around the seal is common. Additionally, after the septum has been pierced by a syringe needle, leakage of volatile materials from the vial is rapid. While this is of little consequence for volatile organic compounds that are sampled and analyzed quickly, it is a serious problem for samples which are used on a long term basis, as is often the case for samples comprising retention time and retention index standards, commonly referred to as markers. While it is possible to replace the crimped septum cap after every use, this approach is inconvenient, time consuming, and costly, and increases the risks of operator exposure to and accidental spillage of the sample. Moreover, leakage around the seal may persist even if the cap is replaced after each use.

Reliable gas chromatographic identification of samples requires the calculation of retention parameters. The calculation of these retention parameters requires that the experimentally-accessible retention parameter, the retention time, $t_r$, be corrected for the gas hold-up (sometimes referred to the dead volume) of the gas chromatographic system, usually represented as $t_m$. Generally, the retention time of an unretained sample component is subtracted from the retention time of a component of interest. When using a thermal conductivity detector, the air or nitrogen peak is often used in this capacity; however, since air does not cause a response in a flame ionization detector, other methods of correcting for gas hold-up have been devised. A number of mathematical techniques require extensive retention time measurements to be conducted on a series of C5–C10 n-alkanes to provide an accurate extrapolation. Other methods of correcting for gas hold-up involve the use of hydrodynamic models of the gas chromatographic column. However, most of these parameters are difficult to measure.

The use of methane as a minimally retained marker is a simple way to approximate gas hold-up under certain conditions, and is especially useful when higher column temperatures (approximately 80–90° C. or higher) are employed with moderately polar to polar open tubular columns. When used properly and under appropriate conditions, the methane marker technique will produce minimal departures from corrections calculated using one of the mathematical approximations.

One conventional technique for delivering methane into a liquid sample, referred to as methanization, is to bubble methane gas into the liquid sample immediately prior to injection of the sample into the chromatographing apparatus. However, this type of methanization suffers from major disadvantages. Methane markers introduced by bubbling methane into a liquid sample will last only a short time (typically 30 minutes or less), and reintroduction of methane into sample vials between chromatographic runs is inconvenient, especially if crimp closure-type automatic sample vials are used. This procedure increases the likelihood of operator exposure to samples. Additionally, bubbling methane through such samples can itself be hazardous and may be impossible to implement in explosion-proof laboratories. Further, if laboratory-utility natural gas is used as a methane source, samples are exposed to numerous non-methane constituents.

The Elahi U.S. Pat. No. 4,131,154 discloses the encapsulation of a sorbent element within a porous filter membrane, and the use of such an element to remove matter from a liquid or gaseous medium. Discrete capsules of the sorbent within an encapsulating membrane are dropped into a vial containing a liquid system and the vial is gently agitated in order to remove the desired matter. Such a system is useful for determining the type or quantities of drugs contained in a biological fluid system, such as blood or urine. However, such a system does not allow for delivery of a marker material such as methane to the fluid system, and neither does it provide for long term storage of samples.

The Graas U.S. Pat. No. 4,270,921 discloses a combination of a microcolumn packed with absorbent material and a centrifuge tube. Centrifugation of the assembly of the microcolumn and the centrifuge tube causes the passage of a predetermined volume of eluant through the microcolumn. While such a system allows for removal of a substance from a fluid, it does not allow for the delivery of a marker such as methane. Such a device still would require transfer of the liquid sample from the centrifuge tube to the sample vial, thereby exposing the operator to the sample, and would solve none of the problems described above which are associated with long term storage of samples within the automatic sampler vials.

The Ullman U.S. Pat. No. 4,624,929 discloses a device for collecting a liquid sample and diluting that sample. The device comprises a housing adapted for mating with a container to form a chamber, and a bibulous pad attached to the housing for collecting a predetermined amount of liquid sample. The device creates a pressure differential sufficient to move a predetermined volume of liquid through the bibulous pad into the housing. Such a device is not capable of delivering a methane marker into a liquid sample system. Additionally, such a device is not suitable as a long term storage container of volatile organic compounds, for such volatile compounds would be lost through the bibulous pad.

The Peterson et. al. U.S. Pat. No. 4,451,374 discloses a method of adding reagent to liquid chromatographic effluents. Hollow fibers are immersed within mobile reagent which permeates through the walls of the fibers and diffuses into the column effluent. While this device is capable of delivering a liquid phase reagent into column effluent, it would not be suitable for delivery of a gaseous marker compound. In addition, such a method requires a large volume of the agent to be introduced, provides no method of sample storage, and exposes the operator to a large volume of reagent.

The prior art offers no solution for the problem of long term storage of volatile organic compounds in commercially available automatic sampler containers, or the problem of long term delivery of marker compounds. Thus, the need remains for devices which will not only allow for long term sample storage and marker compound delivery, but which will also allow for use of small quantities of compounds and which will decrease compound handling and likelihood of operator exposures.

SUMMARY OF INVENTION

Accordingly, it is an object of this invention to obviate the above-described problems. Specifically, it is an object of this invention to provide sample storage devices suitable for long term storage of volatile samples, for example, volatile organic compounds. It is a related object of this invention to provide sample storage devices that minimize sample handling and the risk of operator exposure to the sample and that minimize material loss and allow delivery of a dilute aliquot of sample.

It is another object of this invention to provide marker-containing sample storage devices suitable for introducing a marker such as methane into a sample. It is also an object of this invention to provide marker-containing sample storage devices which minimize the risk of operator exposure to the marker compound or to the sample. It is yet another object of this invention to provide marker-containing sample storage devices which can be reactivated.

It is another object of this invention to provide for combined sample storage and marker compound delivery devices.

In accordance with one embodiment of the present invention, a sample storage device comprises a vial provided with an opening, a permeation tube having a first closed end and an opposite second end, the permeation tube being arranged within the vial, and a septum closure sealing the vial opening. The permeation tube is permeable to a fluid contained in the vial or the permeation tube. In accordance with a more specific embodiment of the present invention, the sample storage device comprises a vial provided with an opening and a permeation tube having a first closed end and an opposite second open end. The permeation tube is arranged within the vial with the second open end of the permeation tube adjacent the vial opening. The device further comprises a septum closure sealing the vial opening and the second open end of the permeation tube. The vial has a sample fluid therein, with at least a portion of the sample fluid being in contact with an outer surface of the permeation tube, and the permeation tube is permeable to the sample fluid.

In another more specific embodiment of the invention, a marker-containing sample storage device comprises a vial provided with an opening and a permeation tube having a first closed end and an opposite second closed end. The permeation tube is arranged within the vial and includes a marker-containing adsorbent therein. The device further comprises a septum closure sealing the vial opening. The vial has a sample fluid therein, and the permeation tube is permeable to the marker. In a further embodiment, the present invention is directed to a marker-containing sample storage device comprising a vial provided with an opening, a permeation tube having a first closed end and an opposite second open end, the permeation tube being arranged within the vial with the second open end of the permeation tube adjacent the vial opening, and a septum closure sealing the vial opening and the opening of the second end of the permeation tube. The vial has a marker-containing adsorbent therein, and the permeation tube contains a fluid sample. At least a portion of an outer surface of the permeation tube is in contact with the marker, and the permeation tube is permeable to the marker.

The use of permeation tubes in the devices and methods of the present invention allows not only long term storage of volatile organic compounds, but also provides storage and delivery of marker compounds. The sample storage devices of the present invention allow for the convenient utilization of commercially available automatic sampler containers, i.e., vials, for long term storage, and have additional advantages of reducing the possibility of operator exposure to the samples and minimizing the quantity of chemicals which must be handled in the laboratory. As retention index standards are usually used at very low concentrations, it is helpful to package standards in a way that facilitates drawing delivery of a very dilute aliquot; the storage devices of the present invention allow for such dilute aliquot delivery and use.

The permeation tubes can be used to form devices which contain high marker capacity adsorbents in which the marker may continuously desorb from the adsorbent into the fluid sample. The marker-containing sample storage devices of the invention may be stored long term with the marker compound being delivered throughout the storage period. These combined sample storage and marker compound delivery devices allow for long term storage and continuous marking of small quantities of dilute chromatographic samples.

These and additional objects and advantages will be more fully apparent in view of the following detailed description.

BRIEF DESCRIPTION OF THE DRAWINGS

The following detailed description may be better understood when viewed in conjunction with the accompanying drawings in which.

DETAILED DESCRIPTION OF THE INVENTION

Figure 1:
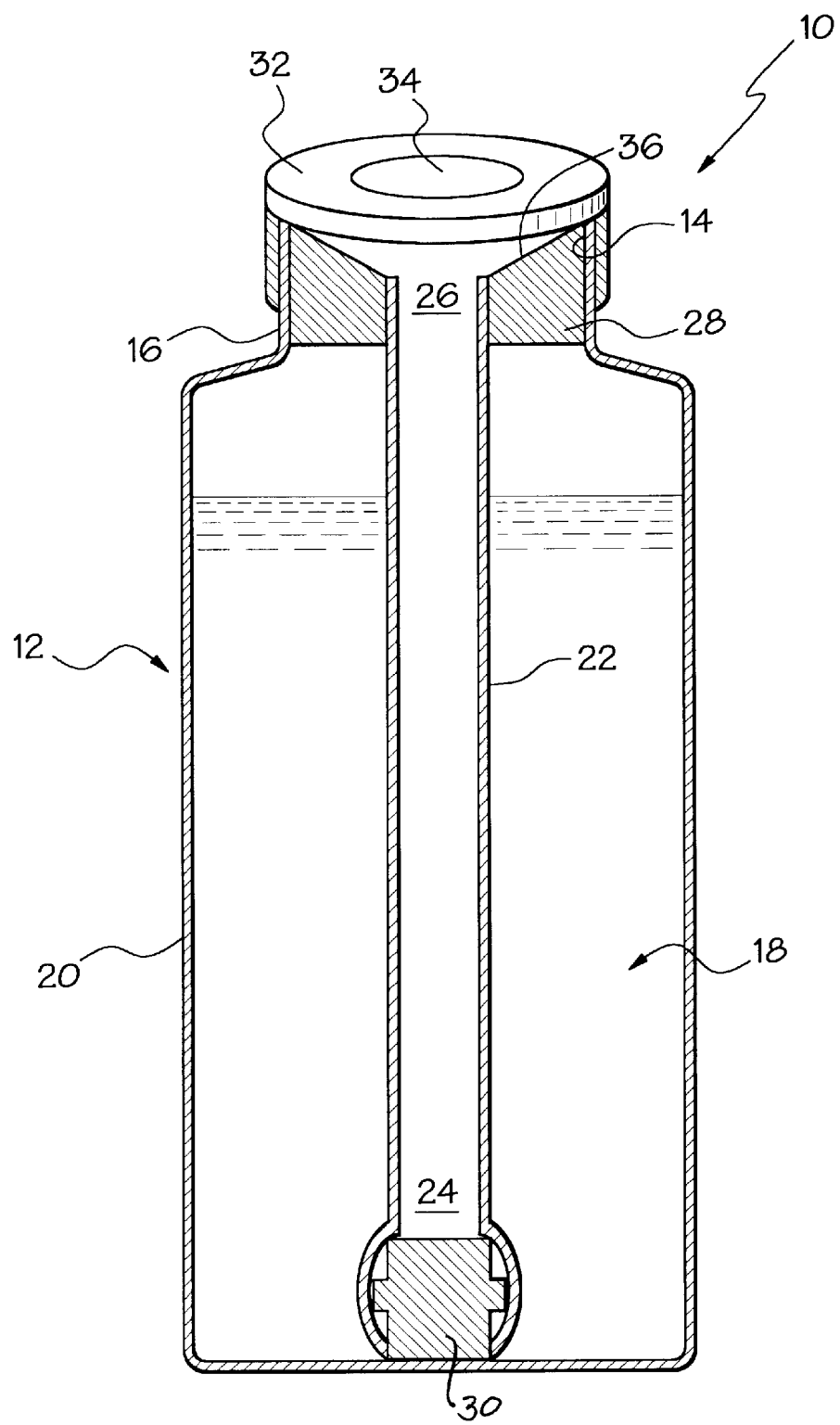
FIG. 1 is a cross-sectional view of a sample storage device made in accordance with one embodiment of the present invention.

Broadly, the sample storage devices according to the present invention comprise a vial provided with an opening, a permeation tube arranged within the vial and having a first closed end and an opposite second end, and a septum closure sealing the vial opening. The permeation tube is permeable to a fluid contained in the vial or the permeation tube. In a more specific embodiment of the present invention, the sample storage devices comprise a vial provided with an opening and a permeation tube having a first closed end and an opposite second open end. The permeation tube is arranged within the vial with the second end of the permeation tube adjacent the vial opening. The devices further comprise a septum closure sealing the vial opening and the second open end of the permeation tube. The vial has a sample fluid contained therein, at least a portion of the sample fluid is in contact with an outer surface of the permeation tube, and the permeation tube is permeable to the sample fluid.

The devices and methods of the invention may also employ a marker in combination with storage of a fluid sample. In one embodiment, the marker-containing sample storage devices comprise a vial provided with an opening, a permeation tube having a first closed end and an opposite second closed end and a septum closure sealing the vial opening. The permeation tube is arranged within the vial and includes a marker-containing adsorbent therein. The vial has a sample fluid contained therein and the permeation tube is permeable to the marker. In another embodiment, the marker-containing sample storage devices comprise a vial provided with an opening, the vial having a marker-containing adsorbent therein, and a permeation tube having a first closed end and an opposite second open end. The permeation tube contains a sample fluid and is arranged within the vial with the second open end of the permeation tube adjacent the vial opening. The device further includes a septum closure sealing the vial opening and the opening of the second end of the permeation tube. At least a portion of an outer surface of the permeation tube is in contact with the marker, and the permeation tube is permeable to the marker.

Referring now to the drawings in detail, like numerals indicate the same elements throughout the views, and elements having the same final two digits (i.e., 12, 212, 312) indicate comparable elements of the various disclosed embodiments.

FIG. 1 illustrates a first embodiment 10 of the sample storage devices of the present invention comprising a vial 12. The vial 12 has an opening 14 and preferably is a standard wide-mouth commercially available automatic sampler vial further comprising a neck 16. The vial 12 has an interior 18 defined by an outer wall 20. Typically, the vial 12 is made of glass, although any suitable material resistant to the sample to be contained therein may be employed.

A permeation tube 22 is arranged in the vial 12. The permeation tube has a first closed end 24 and an opposite, second end 26. In the embodiment of FIG. 1, the second end of the permeation tube is open and the permeation tube is arranged with its second end 26 secured in place in the opening 14 of the vial 12 by a collar 28. The collar 28 is preferably made from a short length of flexible tubing, for example, of elastomeric or rubber material. For example, the collar 28 may be made of polyethylene. In one embodiment, the collar 28 is made of flexible polyethylene tubing having an outer diameter of 0.64 centimeters, an inside diameter of 0.32 centimeters, and a length of 0.48 centimeters, dimensioned to fit a standard automatic sampler vial. The collar 28 is press-fit around the second end 26 of the permeation tube 22. The relative sizes of the collar 28 and the diameter of the opening 14 of the vial 12 preferably provide an interference fit that allows for a seal to the vial 12. An interference fit exists when the outside diameter of the collar 28 exceeds the available diameter of the vial opening 14.

The permeation tube 22 is made of polymeric material through which a fluid may pass at a relatively slow, constant rate at a given temperature. Preferred materials for use in forming the permeation tube include polymers of fluorinated ethylene propylene (FEP Teflon) and polymers of tetrafluoroethylene (TFE Teflon), although other materials suitable for use in forming the permeation tube will be apparent to those skilled in the art in view of the present disclosure. Generally, the TFE Teflon material will provide a higher permeation rate for non halogenated hydrocarbons than will the FEP Teflon material. Branched hydrocarbons generally will have a lower permeation rate in TFE Teflon than straight chain hydrocarbons. These considerations will allow one of ordinary skill in the art to properly choose a permeation tube material.

Generally, the permeation tube is of a short length, such as between about 1 and about 20 centimeters, when employed with a standard automatic sampler vial. In one embodiment, the permeation tube 22 has an outside diameter of 0.48 centimeters, an inside diameter of 0.32 centimeters, and a length of 1.9 centimeters. The lower end 24 of the permeation tube 22 is closed, for example with a disk or plug 30 as shown in FIG. 1. The disk may, for example, be formed of glass-filled Teflon, machined to provide an interference fit with three points of contact as shown in FIG. 1. In one embodiment, the permeation tube inside diameter is 0.32 centimeters, and the glass-filled Teflon plug diameter is 0.4 centimeters. Other embodiments for providing a closed end of the permeation tube will be apparent to those of ordinary skill in the art in view of the present disclosure.

The top of the sample storage device is sealed with a septum closure 32 containing a septum 34 of rubber or the like. In one embodiment, the closure 32 is a standard crimped septum cap and may be removable. In another embodiment which is not shown in the figures, the opening 14 of the vial is threaded and the septum closure 32 is a septum-containing screw-type cap. A syringe needle of a conventional automatic sampler apparatus can pierce the septum 34 during operation. The septum closure seals both the opening 14 of the vial 12 and the second end 26 of the permeation tube 22.

To assemble the sample storage device of FIG. 1, the permeation tube 22 with the plug 30 in its lower end is fit with the collar 28. A fluid sample, preferably a liquid sample of a volatile organic compound, is introduced into the interior 18 of the vial, and the collar 28 is press-fit into the opening 14 of the vial 12 with the permeation tube 22 extending into the interior of the vial 18. The collar 28 may be press-fit into the opening 14 of the vial on a small laboratory hydraulic press or an arbor press. Preferably, the collar 28 and the permeation tube 22 are sized to be flush with the top of the opening of the vial 14, allowing for a standard crimped septum closure 32 to be easily fastened onto the vial. Optionally, before the septum closure 32 is fastened to the opening of the vial 14, a chamfered edge is cut concentrically into the top surface of one or both of the collar 28 and the upper end 26 of permeation tube 22 to help guide a syringe needle into the permeation tube. The chamfered edge may be, for example, at about 30°. This chamfered edge is shown at 36 on collar 28 in FIG. 1, and may be easily cut into the collar and/or the permeation tube with a hand-held carbide cutter of the type commonly used for dressing the ends of tubings in their preparation of packed chromatographic columns.

Preferably, after the septum closure 32 is fastened onto the vial 12 to seal both the vial opening 14 and the open end 26 of the permeation tube 22, the assembled unit is heated, for example in a laboratory oven, and maintained at an elevated temperature, for example, of from about 50 to about 100° C., to allow conditioning and induction of the permeation tube 22 to achieve a constant permeation rate for the fluid sample into the permeation tube. The choice of the induction temperature depends upon the boiling point of the fluid. A typical induction period to achieve a constant permeation rate is approximately 3 weeks. When the sample storage device is used for storage of low concentration retention standards, where a high level of concentration reproducibility is of secondary importance, an induction period of from about 5 to about 7 days may be adequate.

The concentration of the sample in the device can be approximated by Equation (1):

$$[c] = \frac{(v \times 10^6)(T/273)(P/0.101325)q_d}{q_D M} \quad (1)$$

where [c] is the concentration expressed in parts per million (that is, 0.0001 percent), T is the temperature of the permeation tube (in degrees Kelvin), P is the pressure of the diluted fluid (in megapascals), $q_D$ is the volumetric flow-rate or removal rate of the sample (in liters per minute), v is the molar volume of the permeating fluid (in liters) and M is the relative molecular mass of the permeating fluid. A common approximation is to replace v with 22.4 L, the molar volume of an ideal gas. In the embodiment of FIG. 1, the diluted sample vapor is on the inside of the permeation tube. For purposes of Equation 1, the flow rate $q_D$ for the sample storage device is taken as the sampling rate (in microliters per minute), done by syringe on an automatic sampler. This allows the approximate concentration of fluid inside the permeation tube to be calculated.

The sample storage device of the present invention set forth in FIG. 1 is suitable for use within hydrocarbon samples such as n-hexane, n-octane, n-decane, and 2,3-dimethylpentane, as well as halocarbon samples such as fluorotrichloromethane, 1,1-dichloro-1-fluoroethane and 1,2-difluoroethane. The small sample quantity and the minimal sample handling required by this device is particularly useful with respect to compounds such as 1,2-difluoroethane, which is very toxic and of intermediate volatility (normal boiling temperature of 30.7° C.). Such compounds are difficult to handle or store using a conventional automatic sampler vial.

Figure 4:
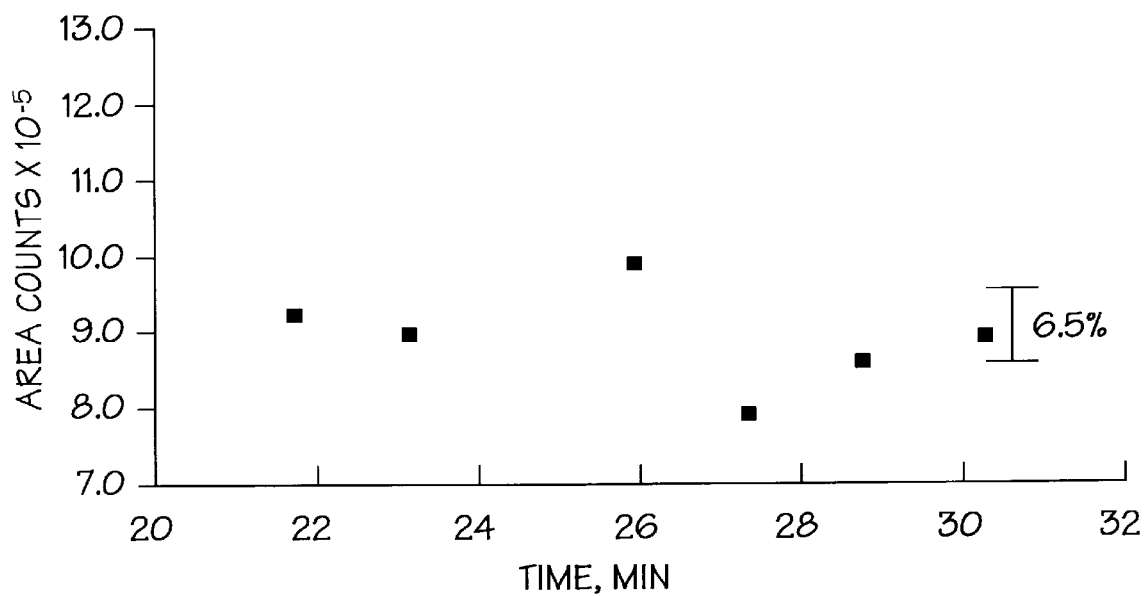
FIG. 4 is a plot of a flame ionization detector (FID) raw area counts against sampling time for n-hexane through a tetrafluoroethylene (TFE) Teflon permeation tube.

Because of differences in permeation rates of different liquids in different permeation tube materials, two different sampling modes exist for use of the present devices. A steady state mode is obtained when the sampling rate (removal of vapor sample) is balanced by the permeation rate (replenishment of fluid). This behavior is illustrated in FIG. 4 in which n-hexane is placed in a sample storage device including a TFE Teflon permeation tube. FIG. 4 shows raw area counts from a flame ionization detector (FID) obtained with seven microliter injections from the interior space of the permeation tube. These samples were injected onto a polymethylsiloxane-coated capillary tube (1 micrometer thickness, 50:1 split ratio). The concentration of samples is approximately constant (within approximately 6.5%) for a sampling rate of approximately one sample every 1.5 minutes. No attempt was made to control the temperature of the vial; temperature control would increase reproducibility of the area measurements, but, as noted earlier, this is of secondary concern for retention index standards.

Figure 5:
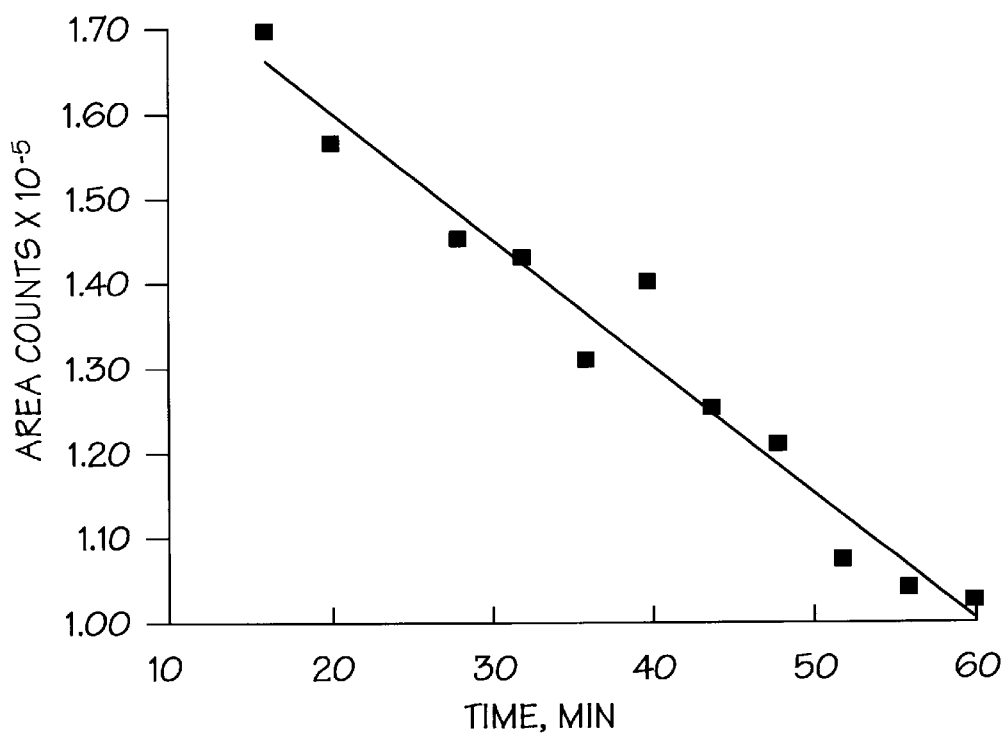
FIG. 5 is a plot of FID raw area counts against sampling time for n-octane through a fluorinated ethylene propylene (FEP) Teflon permeation tube.

A dynamic mode occurs when the sampling rate exceeds the replenishment rate. This behavior is illustrated in FIG. 5, which shows the raw area counts from a flame ionization detector obtained from n-octane placed in a storage device including a FEP Teflon permeation tube. There is a steady decrease in the area counts for a sampling rate of one sample per four minutes. Sampling the interior of the permeation tube at an increasing rate, rather than at a uniform rate, would allow determination of the transition from the steady state mode to dynamic mode. Permeation through the tube at this transition is characteristic for a sample for a given permeation tube material.

An important advantage with regard to the use of the present sample storage devices is the lifetime of the devices. Because of the very low sampling rate used with these devices, lifetime correlations cannot readily be applied. However, based upon gravimetric measurements made on a device prepared with hexane as a sample fluid, used at a typical analytical laboratory sampling rate, the lifetime has been estimated to be approximately three years.

Figure 2:
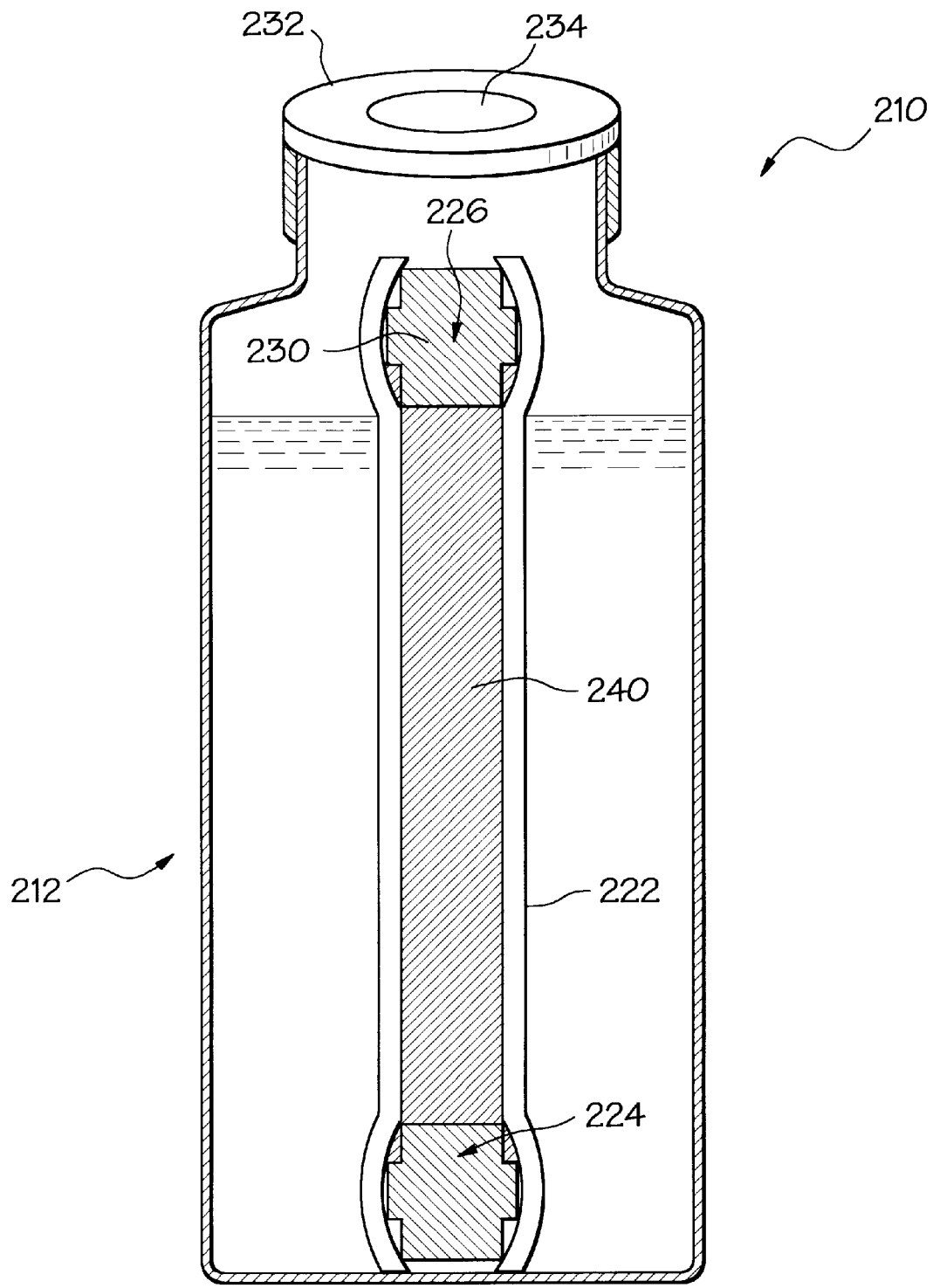
FIG. 2 is a cross-sectional view of a marker-containing sample storage device in accordance with another embodiment of the present invention.

FIG. 2 illustrates a second embodiment of the present invention wherein a marker compound is included in the sample storage device. The device 210 comprises a vial 212 similar to vial 12 described with respect to the embodiment of FIG. 1, and a permeation tube 222 having a first closed end 224 and a second closed end 226. Additionally, the permeation tube 222 contains an adsorbent material 240 having a marker adsorbed thereon within the interior of the tube. In a preferred embodiment, the tube contains a methane-carrying activated carbon adsorbent and serves as a methanizer. The activated carbon adsorbent has an especially high capacity for storing methane.

As in the embodiment of FIG. 1, the permeation tube 222 may be formed of fluorinated ethylene propylene (FEP Teflon) polymer or tetrafluoroethylene (TFE Teflon) polymer. In a preferred embodiment, the tube 222 is made of TFE Teflon tubing with an outside diameter of 0.48 centimeters, an inside diameter of 3.2 centimeters, and a length of 2 centimeters, dimensioned to fit a standard automatic sampler vial. Each end 224 and 226 of the tube 222 is closed, for example, with a small plug 230 as shown in FIG. 2. The plugs 230 may be cylindrical disks of glass-filled Teflon, machined to provide three points of contact as shown in FIG. 2. In one embodiment, the largest diameter of the disk is 0.4 centimeters, providing an interference fit with the tube ends 224 and 226. The interior of the permeation tube 222 contains the adsorbent 240. A preferred activated carbon adsorbent for use as a methanizer is prepared from petroleum coke, and has a measured methane storage capacity of 20.5% (mass-mass) at 4 Mpa and ambient temperature. However, any good quality adsorbent capable of retaining the desired marker compound may be employed.

The permeation tube of FIG. 2 may be prepared by press fitting a glass-filled Teflon plug 230 into one end of the permeation tube 222, and filling the tube through the opposite end with the adsorbent 240. The filled tube is then placed in a small pressure vessel, similar to vessels which are used as sample reservoirs for supercritical fluid chromatography and extraction (SFC/SFE). The adsorbent is charged by introducing the marker compound at ambient pressures. In one embodiment, wherein the marker compound is methane (research grade, 99.99% purity), the adsorbent is charged at approximately 4 MPa (580 psi), at ambient temperature. Lower methane pressures can also be used satisfactorily. After pressurized exposure to the marker compound for a sufficient period of time, for example overnight, the pressure vessel is vented in a fume hood and the open end of the permeation tube is plugged with another Teflon disk 224. The marker-charged permeation tube is then placed in the vial 212 containing a fluid sample, for example a liquid volatile organic sample, and the vial is capped with a septum closure 232 including a septum 234 of rubber. The marker will continuously desorb from the adsorbent and permeate through the permeation tube 222 into the liquid sample. An equilibrium concentration of marker will dissolve in the sample and remain in solution as long as the sample vial is sealed. Marker will also be present in the headspace of the closed vial. Marker that evaporates from the sample or vial during sampling will be replenished from the permeation tube 222 during the useful lifetime of the device.

Figure 3:
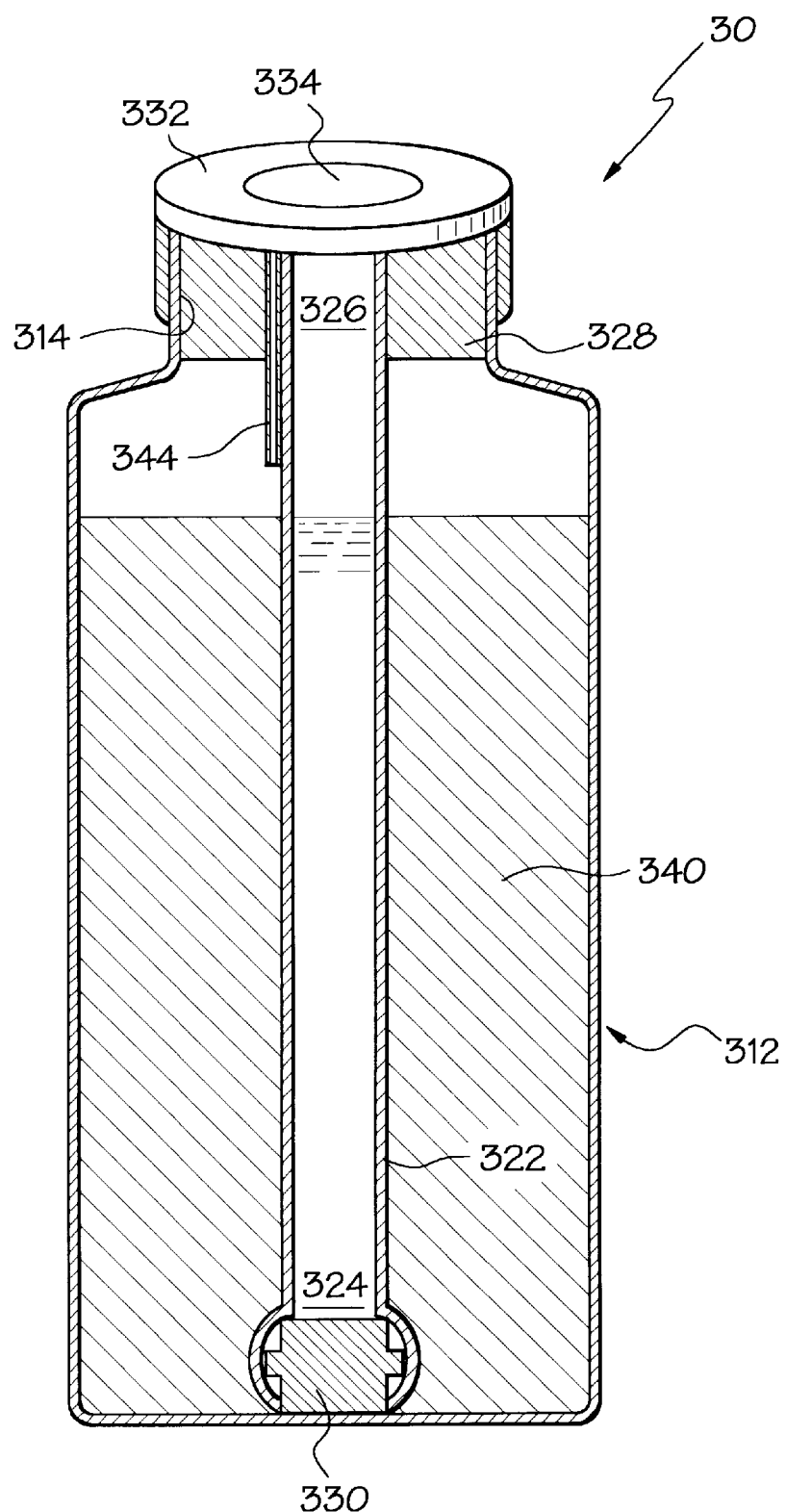
FIG. 3 is a cross-sectional view of a marker-containing sample storage device in accordance with a third embodiment of the present invention.

FIG. 3 illustrates a third embodiment of the present invention comprising an alternate marker-containing sample storage device. The storage device 30 shown in FIG. 3 comprises a vial 312 similar to that described in the embodiment of FIG. 1, and a permeation tube 322. As in the embodiment of FIG. 1, the vial 312 in the embodiment of FIG. 3 preferably is a commercially available automatic sampler vial. The permeation tube 322 has a first closed end 324 and an opposite second open end 326. As in the embodiments of FIGS. 1 and 2, the permeation tube 322 may be formed of fluorinated ethylene propylene (FEP Teflon) polymer or tetrafluoroethylene (TFE Teflon) polymer. In a preferred embodiment, the permeation tube is of TFE Teflon, and has an outside diameter of 0.48 centimeters, an inside diameter of 0.32 centimeters, and a length of 1.9 centimeters.

The permeation tube 322 is arranged in the vial 312 with its second open end 326 adjacent the opening 314 of the vial. Preferably, as shown in FIG. 3, the second end of the permeation tube is secured in the opening 314 of the vial with a collar 328. The collar is preferably formed of an elastomeric or rubber material. In one embodiment, the collar 328 is a polyethylene ring having an outside diameter of 0.64 centimeters, an inside diameter of 0.32 centimeters, and a length of 0.48 centimeters, dimensioned to fit a standard automatic sampler vial. In the embodiment set forth in FIG. 3, the lower end 324 of the permeation tube 322 is closed with a plug 330. The plug 330 is preferably a cylindrical disk of glass-filled Teflon, machined to provide three points of contact, with the largest diameter of the disk being 0.40 centimeters.

Preferably inserted between the collar 328 and the permeation tube 322 is a capillary tube 344 which serves as an inlet for the marker compound in the manufacture of the device, as described in further detail below. In a preferred embodiment, this capillary tube may comprise a single short length of polyamide-coated fused silica capillary tubing. For use with a standard sampler vial, the capillary tube preferably has an outside diameter of 0.32 millimeters, an inside diameter of 0.010 millimeters, and a length of approximately 0.8 centimeters. A capillary with a small inside diameter (such as those used as restrictors in SFC/SFE) is preferred in order to minimize subsequent loss of the marker; however, somewhat larger inside diameters are also satisfactory. Arranged within the vial 312 is an adsorbent material 340. In a preferred embodiment, wherein methane is the marker compound, the adsorbent material is prepared from petroleum coke and has a measured methane storage capacity of 20.5% (mass/mass) at 4 MPa at ambient temperature.

The opening 314 of the vial and the open end 326 of the permeation tube are closed and sealed with a septum closure 332 which has a septum 334. In a preferred embodiment the closure is a removable crimped septum cap.

To assemble the sample storage device of FIG. 3, the collar 328 is placed around the upper end 326 of the permeation tube 322 with the short length capillary tube 344 located between the collar 328 and the permeation tube 322. Both ends of the capillary tube 344 may be trimmed to ensure that any foreign material that may have entered the capillary tube during assembly will not subsequently block the capillary. The upper end of the capillary tube is preferably cut flush with the surface of the upper end 326 of the permeation tube 322 and with the collar 328. The lower end 324 of the permeation tube 322 is fitted with the plug 330, which may be a glass-filled Teflon disk as described earlier. The vial 312 is partially filled (approximately ¾ of the volume of the vial) with the adsorbent 340, and the assembled permeation tube-capillary insert-collar is press fit into the opening 314 of the vial, for example, with a laboratory press or an arbor press. The lower end of the capillary tube 344 is located above the surface of the adsorbent 340.

The sample storage device is activated by placing the device in a pressure vessel and pressurizing with marker compound, as described earlier for the embodiment of FIG. 2. It is preferred that air is purged from the adsorbent space of the vial with an iterative pressurize-and-vent process before the assembly is exposed to the marker compound. After the pressurized exposure, the device may be vented in a fume hood before it is removed. The liquid sample is placed in the interior of the permeation tube 322, and the vial is fit with the septum closure 332. The septum closure seals both the vial opening and the permeation tube. In a preferred embodiment, a crimped septum cap is used. The closure 332 also seals the opening of the capillary 344, and in this way serves the additional role of minimizing marker loss from the adsorbent. The marker will permeate into the space above the fluid sample in the permeation tube.

Marker-containing sample storage devices which utilize high capacity methane adsorbent prepared from petroleum coke can be reactivated by heating. Because some vapors of the sample may permeate into the adsorbent during use of the device, it is important that the adsorbent be reactivated before it is freshly charged with methane. The extent of permeation by the sample vapor can be approximated by using published tables of permeation measurements.

Figure 6:
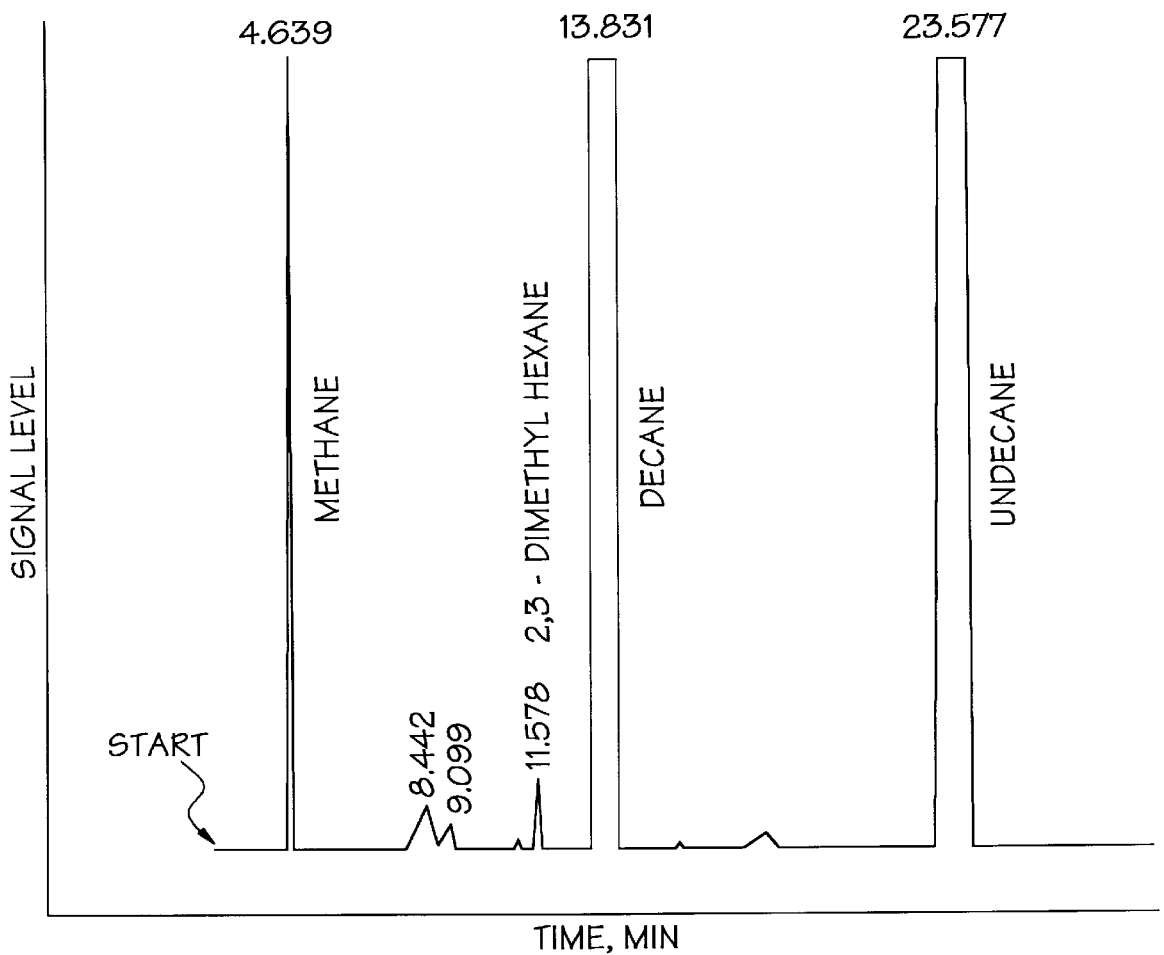
FIG. 6 is a chromatogram of a mixture of surrogate heavy natural gas components obtained from a sample contained in a marker-containing sample storage device according to the present invention.

Both types of marker-containing devices as described herein continue to function until the methane is depleted from the adsorbent. The chromatogram shown in FIG. 6 illustrates a typical response from a marker-containing device. The chromatogram is obtained with a flame ionization detector (FID) for a surrogate mixture of natural gas heavy components, run on a 30 meter capillary column coated with a 5% phenyl polymethylsiloxane having a thickness of 0.1 micron. The first peak corresponds to approximately 2–3 ppm of dissolved methane, the retention time of which is identical to that obtained by pure methane, or for a solution into which methane was freshly bubbled.

When the marker compound delivery devices are used as methanizers, the concentration of methane that can be made available to the sample can be approximated using Equation (2) to estimate an upper bound:

$$[c] = \frac{(v \times 10^6)(T/273)(P/0.101325)q_d}{q_D M} \quad (2)$$

where [c] is the concentration expressed in parts per million (that is, 0.0001 percent), T is the temperature of the permeation tube and fluid (in degrees Kelvin), P is the pressure of the diluted gas stream (in megapascals), $q_D$ is the volumetric flow-rate of the diluent (in liters per minute), v is the molar volume of the permeating fluid (in liters) and M is the relative molecular mass of the permeating fluid. In this case, $q_D$ would be the sampling rate from the sample vial; in practice, however, the solubility of methane in the analyte solution must also be considered. This will generally lower the methane concentration that will be present in the sample.

Having shown and described specific embodiments of the present invention, further adaptions of the device and method described herein can be accomplished by appropriate modifications by one of ordinary skill in the art without departing from the scope of the present invention. A number of alternatives and modifications have been described herein, and others will be apparent to those skilled in the art. Accordingly, the scope of the present invention should be considered in terms of the following claims, and is understood not to be limited to the details of the structures and methods shown and described in the specification and drawings.

What is claimed is:

1. A chromatography marker-containing sample storage device, comprising:
   a vial provided with an opening, the vial having a sample fluid contained therein;
   a permeation tube having a first closed end and an opposite second closed end, the permeation tube being arranged within the vial and including an adsorbent material therein, the adsorbent material having a chromatography marker adsorbed thereon, the chromatography marker comprising methane, the permeation tube being permeable to the chromatography marker such that the sample fluid contains a quantity of the chromatography marker therein; and
   a septum closure sealing the vial opening.

2. A sample storage device according to claim 1, further comprising a collar provided around the second end of the permeation tube and securing the second end of the permeation tube in the opening of the vial.

3. A sample storage device according to claim 2, wherein at least one of the collar and the second end of the permeation tube has a chamfered edge extending into the permeation tube.

4. A sample storage device according to claim 2, wherein the collar is formed of a natural or synthetic plastic or elastomer.

5. A sample storage device according to claim 1, wherein the septum closure comprises a removable crimped septum cap.

6. A chromatography marker-containing sample storage device according to claim 1, wherein the permeation tube is formed of a polymer selected from the group consisting of polytetrafluoroethylene and fluorinated ethylene propylene polymer.

7. A chromatography marker-containing sample storage device according to claim 1, wherein the fluid sample contained in the vial comprises a volatile organic compound.

8. A chromatography marker-containing sample storage device according to claim 1, wherein the adsorbent comprises carbon black.

9. A chromatography marker-containing sample storage device, comprising:
   a vial provided with an opening, the vial having an adsorbent material therein, the adsorbent material having a chromatography marker comprising methane adsorbed thereon;
   a permeation tube having a first closed end and an opposite second end, the permeation tube containing a sample fluid and being arranged within the vial with the second end of the permeation tube adjacent the vial opening and at least a portion of an outer surface of the permeation tube being in contact with the chromatography marker, the permeation tube being permeable to the chromatography marker such that the sample fluid in the permeation tube contains a quantity of the chromatography marker therein; and
   a septum closure sealing the vial opening and the second end of the permeation tube such that access to the sample fluid containing a quantity of the chromatography marker in the permeation tube may be obtained via a septum in the septum closure.

10. A sample storage device according to claim 9, further comprising a collar provided around the second end of the permeation tube and securing the second end of the permeation tube in the opening of the vial.

11. A sample storage device according to claim 10, wherein at least one of the collar and the second end of the permeation tube has a chamfered edge extending into the permeation tube.

12. A sample storage device according to claim 10, further comprising a capillary tube extending from outside the vial through the collar into the vial.

13. A sample storage device according to claim 9, wherein the permeation tube is formed of a polymer selected from the group consisting of polytetrafluoroethylene and fluorinated ethylene propylene polymer.

14. A sample storage device according to claim 9, wherein the fluid sample comprises a volatile organic compound.

15. A sample storage device according to claim 9, wherein the adsorbent comprises carbon black.

* * * * *